United States Patent [19]

Falkowski et al.

[11] 4,093,796

[45] June 6, 1978

[54] ANTIBIOTIC DERIVATIVES OF POLYENE MACROLIDE GROUP AND METHOD OF OBTAINING THE SAME

[75] Inventors: Leonard Falkowski, Gdańsk; Mirosław Bobrowski; Helena Buluk, both of Białystok; Elzbieta Bylec, Gdańsk; Barbara Cybulska; Jerzy Golik, both of Sopot; Paweł Kołodziejczyk, Gdańsk; Jan Pawlak, Gdansk; Andrzej Rudowski, Gdańsk; Jan Zieliński, Gdańsk; Tadeusz Ziminski, Gdynia; Edward Borowski, Gdańsk, all of Poland

[73] Assignee: Politechnika Gdanska, Gdańsk, Poland

[21] Appl. No.: 279,737

[22] Filed: Aug. 10, 1972

[30] Foreign Application Priority Data

Aug. 13, 1971 Poland .................................. 149994
May 4, 1972 Poland .................................. 155167

[51] Int. Cl.$^2$ ............................................. C07H 17/08
[52] U.S. Cl. ..................................... 536/17; 424/180; 536/9
[58] Field of Search ............... 260/210 AB, 211.5 R, 260/211.5 AB; 536/17, 22, 23

[56] References Cited

U.S. PATENT DOCUMENTS

| | | | |
|---|---|---|---|
| 2,736,725 | 2/1956 | Ritter | 260/210 AB |
| 2,852,429 | 9/1958 | Shepler | 260/210 AB |
| 3,244,590 | 4/1966 | Schaffner et al. | 260/210 AB |
| 3,541,079 | 11/1970 | Schramm et al. | 260/211.5 R |

FOREIGN PATENT DOCUMENTS 620,619  8/1961  Belgium .................... 260/210 AB

*Primary Examiner*—Johnnie R. Brown
*Attorney, Agent, or Firm*—Haseltine, Lake & Waters

[57] ABSTRACT

A new class of polyene macrolide antibiotics which exhibit valuable therapeutic properties are obtained by reaction of said antibiotics containing at least one amino group with mono- or oligosaccharides, and/or their derivatives in a suitable solvent.

A series of such have been obtained and examined. They all exhibit a high biological activity and form salts which are soluble in water.

Said sugar derivatives of antibiotics can be used as antifungal agents, also as substances to reduce the overgrowth of the prostrate gland and cholesterol level in the blood.

19 Claims, No Drawings

ANTIBIOTIC DERIVATIVES OF POLYENE MACROLIDE GROUP AND METHOD OF OBTAINING THE SAME

This invention relates to derivatives of polyene macrolide antibiotics the method of their preparation and application.

A wide variety of antibiotics of polyene macrolide antibiotics, are known such as: nystatin, amphotericin B, trichomycin, levorin and others which find a wide practical application in the treatment of mycosis. They are also known for their property to suppressing the overgrowth of the prostate gland and of reducing the cholesterol level in the blood.

One disadvantage of these antibiotics is the lack of adequate water solubility. This is only partly offset by their complexes with sodium desoxycholate and N-acyl derivatives. Another even more essential disadvantage of these substances is that they cannot form a true solution; the substance appears merely to be dispersed as a colloid.

The complex of amphotericin B with sodium desoxycholane, the so called fungizone, brings about a lysis of erythrocites; consequently, organisms treated with this preparation are found to have anaemia. It also contains a constituent not indifferent to the living organism.

N-acyl derivatives likewise exhibit a considerably lower biological activity in relation to the unsubstituted polyenes.

It is an object of the invention to obtain derivatives of polyene macrolide antibiotics exhibiting improved therapeutic properties, especially as regards the treatment of systemic mycosis, also capable of reducing the overgrowth of the prostate gland and the level of cholesterol in blood, as also the elaboration of a method of their preparation.

This object had been achieved by combining at least one amino group in the macrolide molecule, e.g. nystatin, polyfungin, amphotericin B, candicidin, pimaricin, trichomycin, levorin, rimocidin with mono- or oligosaccharides of a series of aldoses or ketoses e.g. glucose, fructose, maltose, ribose, rhamnose and others, and/or with their derivatives e.g. glucuronic acid and bromoacetylglucose.

According to the invention the method of obtaining the derivatives consists in that a polyene macrolide containing at least one amino group in a solvent medium e.g. dimethyl formamide, methanol, dimethylsulphoxide, pyridine, and/or a mixture of solvents in treated with mono- or oligosaccharides of a series of aldoses and ketoses, and/or with their derivatives capable of reacting with an amino group, eventually in the presence of a compound which forms a salt with a molecule of the polyene macrolide derivative, allowed to remain for reaction, then the product of reaction is isolated, and if necessary converted into a salt.

Sugar derivatives of polyene macrolide antibiotics are used as antifungal agents as well as subtances to reduce the overgrowth of the prostate gland and the cholesterol level in blood.

Tne antifungal activity in vitro of the obtained derivatives has been proved by two methods:

(a) determination of the antimicrobial activity of antibiotics and their derivatives in solid nutrient medium—table 1

(b) determination of the antimicrobial activity of antibiotics and their derivatives in liquid nutrient medium—table 2.

The antimicrobial activity in solid nutrient medium has been estimated with the aid of the serial dilution method as follows: 1 mg of antibiotic was dissolved in 1 ml of dimethylsulphoxide and diluted with 9 ml of sterile water. Serial dilutions in water had been performed and the minimum concentration inhibiting the growth of standard strains of *Candida albicans* and *Saccahromyces cerevisiae* estimated: 0.5 ml of the antibiotic solution was mixed in a Petri dish 10 cm in diameter with 9.5 ml of Sabouraud medium having a temperature of about 60° C. After mixing, solidifying the nutrient agar and inoculating the test microorganism on the surface, they were incubated at 36° C for 24 hours. The minimum inhibitory concentration was stated on the basis of observed absence of microorganism growth. Table 1 shows values for nystatin and its glucose derivative:

Table 1

| Preparation | Minimum inhibitory concentration /mcg/ml/ against | |
|---|---|---|
| | Candida albicans | cerevisiae |
| nystatin | 2 | 2 |
| glucose derivative of nystatin | 2 | 2 |

The antimicrobial activity of antibiotics and their derivatives in liquid nutrient medium has been determined by making serial dilutions of antibiotics in the manner described above and by mixing of 0.5 ml of antibiotic solution with 4.5 ml of medium inoculated with tested microorganisms and prepared after Sabouraud without agar and with the addition of tarchocilin in the amount of 25 mg per 1 l. Solutions were allowed to stand for 48 hours at the temperature of 32° C.

Minimum concentration that inhibits the microorganisms growth has been determined on the basis of turbidity determined by extinction growth at 660 mm; results are compared in table 2.

Table 2

| Item | Antibiotic | MIC /mcg/ml/ | Derivatives | MIC /mcg/ml/ |
|---|---|---|---|---|
| 1 | pimaricin | 2.5 | NGL pimaricin | 5.0 |
| 2 | rimocidin | 2.5 | NGL rimocidin | 2.5 |
| 3 | nystatin $A_1$ | 0.5 | NGL nystatin $A_1$ | 1.0 |
| | | | NML nystatin $A_1$ | 2.5 |
| | | | NRL nystatin $A_1$ | 2.0 |
| 4 | polifungin | 0.5 | NGL polifungin | 1.0 |
| 5 | amphotericin B | 0.05 | NGL amphotericin B | 0.2 |
| | | | NGL amphotericin B | 0.5 |
| 6 | candidin | 0.2 | NGL candidin | 1.0 |
| 7 | mycoheptin | 2.5 | NGL mycoheptin | 2.5 |
| 8 | candicidin | 0.001 | NGL candicidin | 0.005 |
| 9 | trichomycin | 0.001 | NGL trichomycin | 0.005 |
| 10 | levorin | 0.05 | NGL levorin | 0.2 |
| 11 | aureofacin | 0.005 | NGL aureofacin | 0.025 |
| | | | NGU aureofacin | 0.025 |

MIC - minimum inhibitory concentration
NGL - glucose derivative
NML - maltose derivative
NRL - ribose derivative
NGU - glucuronic derivative It is evident from the above designations that antifungal activity of derivatives of polyene macrolide antibiotics is of the same order as that of initial antibiotics.

Studies were also conducted on the activity of the glucose derivative of nystatin, as compared with nystatin, in relation to a series of pathogenic strains of Candida and Geotrichum isolated from contaminated human members. These investigation results are shown in table 3. The acute toxity ($LD_{50}$) of two glucose preparations of the polyfungin derivative was estimated on mice weighing about 24 g.

The antibiotic was administered to the animals intraperitoneally in physiological sodium chloride solution in the amount of 1.0 ml. Acute toxicity of the sodium salt and the glucose imidazole salt of the polyfungin derivative was compared. Both preparations were administered to mice on time in the following dosages: 4 mg/kg, 12 mg/kg, 36 mg/kg, 80 mg/kg and 300 mg/kg of body weight. There were six mice in each group.

imidazole salt seems to exhibit more toxicity after 48 hours of observation.

Toxicity—according to Berents scale—is 54.7 mg/kg for the sodium salt of glucose derivative of polyfungin, 52.5 mg/kg for imidazole salt.

The in vivo antifungal activity of insoluble polyfungin and the water soluble sodium salt of the glucose derivative of polyfungin were compared on the basis of experiments carried out on white mice race "Porton" weighing about 50 g. Mice were infected intravenously with the Candida albicans strain No. 4477 by administering to the tail vein 0.2 ml of the suspension containing Table 3

| Micro-organisms | Number of strains studied | Number of strains the growth of which has been inhibited by the action of | | | | | | | | | | |
|---|---|---|---|---|---|---|---|---|---|---|---|---|
| | | Nystatin /mcg/ml/ | | | | | | Glucose derivative of nystatin /mcg/ml/ | | | | |
| | | 1.56 | 3.12 | 6.25 | 12.5 | 25.0 | 50.0 | 3.12 | 6.25 | 12.5 | 25.0 | 50.0 |
| Candida albicans after 24 hrs | 12 | 1 | 11 | 0 | 0 | 0 | 0 | 1 | 11 | 0 | 0 | 0 |
| Candida albicans after 48 hrs | 12 | 0 | 2 | 10 | 0 | 0 | 0 | 0 | 0 | 12 | 0 | 0 |
| Candida sp. after 24 hrs | 8 | 2 | 3 | 1 | 2 | 0 | 0 | 2 | 5 | 0 | 1 | 0 |
| Candida sp. after 48 hrs | 8 | 0 | 3 | 1 | 3 | 1 | 0 | 0 | 2 | 3 | 2 | 1 |
| Geotrichum sp. after 24 hrs | 12 | 0 | 2 | 10 | 0 | 0 | 0 | 0 | 5 | 7 | 0 | 0 |
| Geotrichum sp. after 48 hrs | 12 | 0 | 0 | 5 | 7 | 0 | 0 | 0 | 0 | 9 | 3 | 0 |

After 24 hrs and 48 hrs since injection the number of dead animals was noted and the cumulative percentage of dead and surviving animals was calculated. Next, the $LD_{50}$ was determined by probite method. Results are shown in table 4.

Table 4

| Dosis of antibiotics in mg/kg | Number of animals put to death under the action of glucose derivative of polifungin | | | |
|---|---|---|---|---|
| | Observation after 24 hrs | | Observation after 48 hrs | |
| | Sodium salt | Imidazole salt | Sodium salt | Imidazole salt |
| 4 | 0 | 0 | 0 | 0 |
| 12 | 0 | 0 | 1 | 0 |
| 36 | 0 | 0 | 0 | 2 |
| 60 | 0 | 0 | 0 | 0 |
| 80 | 3 | 3 | 4 | 3 |
| 100 | 4 | 3 | 5 | 5 |
| 300 | 6 | 6 | 6 | 6 |
| $LD_{50}$ | 85 mg/kg | 89 mg/kg | 80 mg/kg | 74 mg/kg |

Acute toxicity of sodium and imidazole salts of both glucose derivatives of polifungin in terms of $LD_{50}$ is similar and varies somewhere in the neighborhood of 80 mg of preparation per kg of weight. The sodium salt is somewhat more toxic when determining the dosage after 24 hours of observation of polyfungin whereas the $3 \times 3 \times 10$ cells of Candida albicans obtained from 48 hours culture on Sabouraud agar.

The preparation of the sodium salt of the glucose derivative of polyfungin was dissolved in 0.9% sodium chloride solution whereas the insoluble polyfungin was suspended in the same solution. Both antibiotics were administered every day to the mice intraperitoneally in the amount of 0.5 ml solution throughout the entire experimental period. The following dosages of antibiotics were administered: 1 mg/kg, 2 mg/kg, 4 mg/kg, 8 mg/kg, 16 mg/kg, of body weight. There were 6 mice in each group.

Beginning with the fourth day of injection, every second day a mouse from each group was put to death by breaking the spinal cord, dissected and the number of cells Candida albicans in 1 g of kidney determined.

The kidneys were weighed and homogenized in bacteriological glass mortars and the obtained homogenates diluted serially with physiological sodium chloride solution, then 0.1 ml of each homogenate as also dilutions were inoculated on the solid Sabouraud base. After 48 hours of incubation at the temperature of 30° C the developed colonies were counted and the number of the cells Candida albicans contained in 1 g of kidney of the animal were calculated. Investigation results are shown in Table 5.

Table 5

| Antibiotic | Daily dosage of antibiotic in mg/kg | Day since infection | | | | | |
|---|---|---|---|---|---|---|---|
| | | 4 | 6 | 8 | 10 | 12 | 14 |
| | | Number of Candida albicans cells per 1 g of kidney | | | | | |
| Glucose derivative of polifungin | 0 | $8.0 \times 10^4$ | $1.9 \times 10^4$ | $1.8 \times 10^6$ | $5.0 \times 10^7$ | $1.4 \times 10^7$ | $1.0 \times 10^6$ |
| | 1 | $4.5 \times 10^4$ | $5.3 \times 10^4$ | $7.6 \times 10^6$ | $1.4 \times 10^6$ | $2.4 \times 10^7$ | $1.9 \times 10^6$ |
| | 2 | $1.0 \times 10^4$ | $1.6 \times 10^5$ | $3.5 \times 10^5$ | $1.0 \times 10^5$ | $1.0 \times 10^6$ | $4.9 \times 10^5$ |
| | 4 | $2.0 \times 10^4$ | $3.0 \times 10^4$ | $1.2 \times 10^4$ | $2.9 \times 10^4$ | $1.1 \times 10^3$ | $4.2 \times 10^4$ |
| | 8 | $1.1 \times 10^4$ | $1.3 \times 10^3$ | 0 | $2.5 \times 10^4$ | 0 | 0 |
| | | $9.5 \times 10^3$ | 0 | 0 | 0 | 0 | 0 |
| | 1 | $3.3 \times 10^4$ | $8.2 \times 10^5$ | $7.9 \times 10^4$ | $6.2 \times 10^6$ | $1.4 \times 10^5$ | $5.2 \times 10^6$ |

Table 5-continued

| Antibiotic | Daily dosage of antibiotic in mg/kg | Day since infection | | | | | |
|---|---|---|---|---|---|---|---|
| | | 4 | 6 | 8 | 10 | 12 | 14 |
| | | Number of Candida albicans cells per 1 g of kidney | | | | | |
| | 2 | $1.7 \times 10^6$ | $8.2 \times 10^5$ | $2.3 \times 10^5$ | $1.7 \times 10^6$ | $2.6 \times 10^6$ | $4.3 \times 10^5$ |
| | 4 | $8.6 \times 10^5$ | $4.4 \times 10^5$ | $1.0 \times 10^4$ | $4.1 \times 10^3$ | $1.5 \times 10^6$ | $1.2 \times 10^6$ |
| poli- | 8 | $2.2 \times 10^4$ | $3.7 \times 10^4$ | $3.7 \times 10^3$ | $6.4 \times 10^4$ | $6.3 \times 10^4$ | $1.3 \times 10^3$ |
| fungin | 16 | $2.0 \times 10^6$ | $3.9 \times 10^4$ | $3.9 \times 10^3$ | $4.3 \times 10^3$ | $1.1 \times 10^4$ | $3.6 \times 10^3$ |

It follows from investigation results that the sodium salt of the glucose derivative of polyfungin dissolved in water exhibits much higher activity in vivo than the parent antibiotic in the treatment of mice with generalized subacute candidiasis.

After application of the soluble glucose derivative of polyfungin in the amount of 8–16 mg/kg a complete sterilization of mouse kidneys can be achieved. After application of insoluble polyfungin one such effect could not be observed.

An advantage of the sugar derivatives of polyene macrolides developed by combination of these antibiotics with mono- and oligosaccharides and their derivatives is their readiness for dispersion in water; in the case of polyene macrolides and their derivatives possessing an acid-group—their ability to form, in an almost neutral medium, solid salts with cations, which are very easily soluble in water.

Various derivatives of various polyene macrolides and various sugars and their salts with cations dissolve in water and form solutions comprising to a different degree largely dispersed colloids and true solutions. A great many of such substances such as the sodium salt of the glucose or maltose derivative of nystatin form true solutions free of colloids. Such soluble and stable sugar derivatives of polyene macrolides and their salts exhibit high biological activity. Their microbiological spectrum is identical with that of the initial antibiotics.

The reaction of polyene macrolides containing an amino group with sugar proceeds gently even without using a catalyst which when applied only speeds up the reaction process; on the other hand, taking into consideration the easy reaction of sugars with the amino groups of polyene macrolides it is not necessary to previously activate the reacting sugar.

The method of preparation of sugar derivatives of polyene macrolides and their purification is presented by way of examples stated below:

EXAMPLE I 3.0 g of nystatin ($E_{1\ cm}^{1\%} = 560$ at 304 nm), 3.0 g of glucose and 0.5 g of imidazole are dissolved in 50 ml of dimethyl formamide allowed to stand in the thermostat at the temperature 36° for 2 days. At this time practically all antibiotics will react. The obtained derivative and unreacted glucose will be precipitated by means of ethyl ether, washed with solvent and dried in vacuo. The obtained crude derivative in the form of the imidazole salt weighs 6.1 g and exhibits $E_{1\ cm}^{1\%} = 260$ at 340 nm.

EXAMPLE II 3.0 g of nystatin $E_{1\ cm}^{1\%} = 560$ at 304 nm) and 3.0 g of glucose are dissolved in 50 ml of dimethyl formamide and is allowed to stand at the temperature of 30° C for 2 days. Further procedure according to example I. The obtained product weighs 5.6 g of crude glucose derivative and exhibits $E_{1\ cm}^{1\%} = 280$ at 304 nm.

EXAMPLE III 10.0 g of polyfungin ($E_{1\ cm}^{1\%} = 825$ at 304 mn) is dissolved in 50 ml of dimethyl formamide, then 3.0 g of glucose and 0.1 g of ascorbic acid are added; the mixture is allowed to stand in the thermostat at the temperature of 36° C for 2 days. Further procedures as given in example I. The obtained product weighs 12.9 g of crude derivative with $E_{1\ cm}^{1\%} = 570$ at 304 nm.

EXAMPLE IV 0.5 nystatin ($E_{nystatin(XE1\ cm}^{1\%} = 640$ at 304 nm) and 0.5 g of maltose are dissolved in 20 ml of dimethyl formamide and allowed to stand at the temperature of 36° C for 2 days. Further procedure as given in example I. Obtained will be 0.9 of crude derivative with $E_{1\ cm}^{1\%} = 310$ at 304 n.

EXAMPLE V 1.0 g of amphotericin B($E_{1\ cm}^{1\%} = 1420$ at 382 nm) and 0.3 g of glucose in suspended in 20 ml of dimethyl formamide and allowed to remain for 2 days at the temperature of 36° C. Further procedure as given in example 1. Obtained will be 1.3 g of crude derivative with $E_{1\ cm}^{1\%} = 1050$ at 382 nm.

EXAMPLE VI 1.0 g of amphotericin B($E_{1\ cm}^{1\%} = 1420$ at 382 nm) and 0.6 g of maltose in 20 ml of dimethyl formamide are allowed to remain for 2 days at the temperature of 36°. Further procedure as given in example I. Obtained will be 1.5 g of crude derivative with $E_{1\ cm}^{1\%} = 9.60$ at 382 nm.

EXAMPLE VII 1.0 g of candicidin ($E_{1\ cm}^{1\%} = 430$ at 378 nm) and 1.0 g of glucose and 0.05 g of imidazole are dissolved in 50 ml of pyridine and allowed to remain at room temperature in darkness for 7 days. Further procedure as given in example I. Obtained will be 2.1 g of crude derivative in the form of salt with organic base with $E_{1\ cm}^{1\%} = 200$ at 378 nm.

EXAMPLE VIII 0.5 g of candicidine ($E_{1\ cm}^{1\%} = 750$ at 378 nm) and 0.39 of maltose is dissolved in 10 ml of dimethyl formamide and incubated at the temperature 36° for 2 days. Further procedure as given in example I. Obtained 0.7 g of raw derivative with $E_{1\ cm}^{1\%} = 410$ at 378 nm.

EXAMPLE IX 0.5 g of pimaricin ($E_{1\ cm}^{1\%} = 800$ at 304 nm), 0.5 g of ribose and 0.5 g of imidazole are dissolved in 100 ml of methanol and allowed to remain at the temperature of 36° for 24 hours, next the methanol evaporated in vacuo up to 10 ml, and the crude derivative precipitated and washed with ethyl ether. Obtained will be 1.0 g of raw substance with $E_{1\,cm}^{1\%} = 340$ at 304 nm, in the form of salt with imidazole.

EXAMPLE X 1.0 g of pimaricin with $E_{1\,cm}^{1\%} = 800$ at 304 nm and 0.6 g of maltose are dissolved in 200 ml of dimethyl formamide and allowed to remain at the temperature 36° for 2 days. Further procedure as given in example I. Obtained will be 1.4 g of raw derivative with $E_{1\,cm}^{1\%} = 530$ at 304 nm.

EXAMPLE XI 0.5 g of polifungin ($E_{1\,cm}^{1\%} = 700$ at 304 nm), 0.5 g of maltose and 0.1 g of imidazole are dissolved in 20 ml of dimethyl formamide at the temperature of 36° for 2 days. Further procedure as given in example I. Obtained will be 1.1 g of crude derivative in the form of the salt with imidazole with $E_{1\,cm}^{1\%} = 318$ at 304 nm.

EXAMPLE XII 0.5 g of trichomycin ($E_{1\,cm}^{1\%} = 500$ at 378 nm) and 0.15 g of glucose are dissolved 0.8 ml of dimethyl formamide and is allowed to remain at the temperature of 36° for 2 days. Further procedure as given in example I. Obtained will be 0.55 g of crude derivative with $E_{1\,cm}^{1\%} = 360$ at 378 nm.

EXAMPLE XIII 1.0 g of trichomycin with $E_{1\,cm}^{1\%} = 500$ at 378 nm and 0.6 g of maltose are dissolved in 20 ml of dimethyl sulfoxide and allowed to remain at the temperature of 36° for 2 days. Further procedure as given in example I. Obtained will be 1.4 g of crude derivative with $E_{1\,cm}^{1\%} = 320$ at 378 nm.

EXAMPLE XIV 0.5 of pimaricin ($E_{1\,cm}^{1\%} = 600$ at 304 nm), 0.5 g of fructose and 0.1 g of imidazole dissolved in 20 ml of methanol and dimethyl formamide mixture, ratio 2:1, and is allowed to remain for 2 days at the temperature of 36°. Further procedure as given in example I. Obtained will be 1.0 g of crude derivative in the form of the salt with imidazole with $E_{1\,cm}^{1\%} = 370$ at 304 nm.

Example XV 0.1 g of levorin ($E_{1\,cm}^{1\%} = 800$ at 378 nm) and 0.1 g of glucose are dissolved in 2.0 ml of dimethylformamide and allowed to remain at the temperature of 36°. Further procedure as given in example I. Obtained will be 0.2 g of crude derivative with $E_{1\,cm}^{1\%} = 370$ at 378 nm.

EXAMPLE XVI 0.5 g of levorin ($E_{1\,cm}^{1\%} = 800$ at 378 nm) and 0.3 g of maltose are dissolved in 20 ml of pyridine and dimethyl formamide mixture (ratio 2:1) and allowed to remain at the temperature of 36° for 2 days. Further procedure as given in example I. Obtained will be 0.7 g of crude derivative with $E_{1\,cm}^{1\%} = 520$ at 378 nm.

EXAMPLE XVII 1.0 g of rimocidin ($E_{1\,cm}^{1\%} = 500$ at 304 nm), 1.0 g of glucose and 0.2 g of imidazole are dissolved in 15 ml of dimethyl formamide and allowed to remain at the temperature of 36° for 2 days. Further procedure as given in example I. Obtained will be 2.0 g of crude derivative with $E_{1\,cm}^{1\%} = 230$ at 304 nm.

EXAMPLE XVIII 1.0 g of crude glucose derivative of candicidin in the form of the salt with imidazole, as obtained in example VII, is dissolved in 20 ml of water and after acidifying with acetic acid is shaken with 20 ml of butanol. After the layers have been allowed to settle, the water layer is removed while the remaining butanol layer containing the antibiotic derivative is washed several times with water saturated with butanol and acidified with acetic acid using 10 ml portions, until the imidazole is completely removed. The remaining butanol solution of the glucose derivative of candicidin, after being liberated from the imidazole salt is concentrated in vacuo until water is completely removed azeotropically. The derivative is precipitated from the remaining solution with ethyl ether, the precipitate washed with this solvent and dried in vacuo. Obtained will be 0.5 g of the product not containing imidazole with $E_{1\,cm}^{1\%} = 300$. In the same manner are liberated from the imidazole salt the sugar derivatives of the remaining polyene macrolides.

EXAMPLE XIX 10 g of crude product obtained from the reaction of nystatin with glucose (Example II) is dissolved in 100 ml of the mixture: ethyl acetate, butanol, methanol and water (20:15:15:35). The solution is filtered through ulite layer and loaded to five elements of the countercurrent distribution apparatus, after this 100 transfers of upper phase and alternate 50 transfers of upper and lower phase are performed. The position of the antibiotic substance is determined on the basis of light absorption measurement at 304 nm, after having previously diluted with methanol the samples of the upper phase. From elements that correspond to the drawing of the current distribution curve of the antibiotic purified substance is isolated by distilling off the solvents with the addition of butanol to a small volume in vacuo and precipitated from remnants with ethyl ether. The precipitate is washed with ether ethyl and dried in vacuo. Obtained is 1.5 g of preparation with $E_{1\,cm}^{1\%} = 720$ at 304 nm.

EXAMPLE XX 200 mg of the glucose derivative of candicidin obtained in example XVIII is dissolved in 2.0 ml of the mixture of chloroform, methanol and water (10:5:1), and is distributed on a column filled with 7.0 g of Sephadex LH-20; the antibiotic effluent curve is determined on the basis of light absorption measurement at 378 nm. The purified antibiotic is isolated from the effluent by evaporating the solvent in vacuo with the addition of butanol, precipitating with ethyl ether, washing the precipitate with ether and drying in vacuo. Obtained will be 60 mg of product with $E_{1\,cm}^{1\%} = 700$.

EXAMPLE XXI 0.5 g of the crude glucose derivative of nystatin as obtained in example II is purified by the method of distribution chromatography on a column with silica gel, grain size below 0.08 nm, saturated with water in the ratio 1:1, while using the solvent mixture, chloroform, methanol, water in the ratio 10:10:3. The antibiotic effluent curve from the column is determined by measuring light absorption at 304 nm. The purified antibiotic is isolated from the effluent by evaporating the solvents in vacuo with the an addition of butanol, precipitating with ethyl ether, washing the precipitate with this solvent and drying in vacuo. Obtained will be 0.12 g of preparation with $E^{1\%} = 715$ at 304 nm.

EXAMPLE XXII 0.5 g of purified glucose derivative of nystatin obtained in example XIX is added to 10 ml of water and while being thoroughly mixed and cooled outside with an ice bath, is neutralized with sodium bicarbonate solution and lyophilized. Obtained will be 0.5 g of sodium salt of the glucose derivative of the nystatin with $E_{1\ cm}^{1\%} = 710$ at 304 nm.

EXAMPLE XXIII 0.5 g of glucose derivative of the amphotericin B obtained in example V and purified according to the method described in example XIX with $E_{1\ cm}^{1\%} = 1370$ is dispersed in 10 ml of water and while cooling from outside with ice and thorough mixing is neutralized to pH = 7.2 by means of 0.1 N of an aqueous solution of sodium hydroxide and lyophilized. Obtained will be 0.5 g of the sodium salt of the glucose derivative of amphotericin B with $E_{1\ cm}^{1\%} = 1335$ at 382 nm.

EXAMPLE XXIV 1.0 g of pimaricin with $E_{1\ cm}^{1\%} = 800$ at 304 nm and 0.6 g of rhamnose are dissolved in 100 ml of methanol and allowed to remain at the temperature of 36° for 2 days. Methanol is evaporated to the volume of about 10 ml and the crude derivative is isolated by precipitating and washing with ethyl ether. Obtained will be 1.5 g of derivative with $E_{1\ cm}^{1\%} = 550$ at 304 nm.

EXAMPLE XXV 1.0 g of pimaricin with $E_{1\ cm}^{1\%} = 800$ at 304 nm and 0.6 g of 6-acetylglucose are dissolved in 100 ml of methanol and allowed to remain at the temperature of 36° for 2 days. Further procedure as given in example XXIV. Obtained will be 1.55 g of the crude derivative with $E_{1\ cm}^{1\%} = 540$ at 304 nm.

EXAMPLE XXVI 1.5 g of the sugar derivative of antibiotic is suspended in 20 ml of the water, 10 mg of imidazole added, filtered through Sephadex G-15 lyophilized.

EXAMPLE XXVII 1 g of sugar derivative of antibiotics is suspended in 20 ml, added 84 ml of sodium bicarbonate solution or 100 mg of imidazole added, water is evaporated with butanol in vacuo and the salt of the antibiotic derivative precipitated with ether.

EXAMPLE XXVIII 1 g of the sugar derivative of the antibiotics is suspended in 20 ml of water, 120 mg of 2- amino-2(hydroxymethyl)-propane -1,3 -diol, filtered through Sephadex G-15 and lyophilized.

EXAMPLE XXIX 1 g of the sugar derivative of the antibiotics is suspended in 20 ml of water, 84 mg of acid sodium carbonate or 100 mg of imidazole added, water is distilled under reduced pressure with butanol and the salt of the derivative isolated with dry ethyl ether.

EXAMPLE XXX 200 mg of aureofacin and 50 g of glucuronic acid are suspended in 10 ml of dimethyl formamide and allowed to remain at the temperature of 32° for one night. The insoluble substance is centrifuged and the antibiotic precipitated with dry ethyl ether. Obtained will be 110 mg of the glucuronic derivative with $E_{1\ cm}^{1\%} = 370$ at 380 nm.

EXAMPLE XXXI 200 mg of amphotericin B and 50 mg of glucuronic acid are suspended in 10 ml of dimethyl formamide and allowed to remain at the temperature of 32° C. The derivative is precipitated with dry ethyl ether. Obtained will be 240 mg of the glucuronic derivative with $E_{1\ cm}^{1\%} = 940$ at 382 nm.

EXAMPLE XXXII 200 mg of polyfungin and 50 mg of glucuronic acid is suspended in 10 ml of dimethyl formamide and allowed to remain at the temperature of 32° C for one night. The derivative is precipitated with dry ethyl ether. Obtained will be 156 mg of the glucuronic derivative with $E_{1\ cm}^{1\%} = 480$ at 304 nm.

EXAMPLE XXXIII 100 mg of perimicin with $E_{1\ cm}^{1\%} = 710$ at 380 nm is dissolved in 5 ml of dimethyl formamide, 30 mg of D-glucuronic acid added and allowed to remain at the temperature of 38° C for 24 hrs. The crude derivative is precipitated with 100 ml of dry ethyl ether. Obtained will be 100 g of a substance with $E_{1\ cm}^{1\%} = 690$ at 380 nm.

We claim:

1. The N-glycosyl reaction product of an amino group-containing polyene macrolide antibiotic obtained by reacting said antibiotic with a saccharide selected from the group consisting of aldose monosaccharides, ketose monosaccharides, aldose oligosaccharides and oligosaccharides. oligosacharides.

2. The product according to claim 1 wherein the polyene macrolide antibiotic is selected from the group consisting of pimaricin, rimocidin, nystatin, polyfungin, amphotericin B, candidin, mycoheptin, candicidin, trichomycin, levorin and aurofacin.

3. The product according to claim 2 wherein the saccharide is selected from the group consisting of glucose, matlose, ribose, fructose, rhamnose, glucuronic acid, acetylglucose and bromoacetylglucose.

4. The product according to claim 3 which is glucosyl pimaricin.

5. The product according to claim 3 which is glucosyl mystatin.

6. The product according to claim 3 which is glucosyl polyfungin.

7. The product according to claim 3 which is glucosyl amphotericin B.

8. The product according to claim 3 which is glucosyl mycoheptin.

9. The product according to claim 3 which is glucosyl candicidin.

10. The product according to claim 3 which is glucosyl trichomycin.

11. The product according to claim 3 which is glucosyl levorin.

12. The product according to claim 3 which is glucosyl aureofacin.

13. The product according to claim 3 which is glucosyl perimycin.

14. The product according to claim 3 wherein the antibiotic is nystatin.

15. A method of preparing the reaction product according to claim 1 comprising reacting said antibiotic with said saccharide in a solvent and isolating the reaction product.

16. A method according to claim 15 wherein the solvent is selected from the group consisting of dimethylformamide, methanol, dimethylsulfoxide and pyridine and mixtures thereof.

17. A method according to claim 15 wherein the reaction is carried out in the presence of a base which forms a salt with the reaction product.

18. A method according to claim 15 which further comprises reacting the reaction product with a base which forms a salt with said reaction product.

19. A method according to claim 18 wherein the salt-forming base is selected from the group consisting of sodium carbonate, sodium hydroxide, imidazole and 2-amino-2(hydroxymethyl) propane-1,3-diol.

* * * * *